United States Patent
Weckstrom et al.

(10) Patent No.: US 8,642,966 B2
(45) Date of Patent: Feb. 4, 2014

(54) GAS ANALYZER FOR MEASURING AT LEAST TWO COMPONENTS OF A GAS

(75) Inventors: Kurt Peter Weckstrom, Esbo (FI); Heikki Antti Mikael Haveri, Huhmari (FI)

(73) Assignee: General Electric Company, Schenectady, NY (US)

(*) Notice: Subject to any disclaimer, the term of this patent is extended or adjusted under 35 U.S.C. 154(b) by 31 days.

(21) Appl. No.: 13/280,852

(22) Filed: Oct. 25, 2011

(65) Prior Publication Data
US 2012/0097852 A1 Apr. 26, 2012

(30) Foreign Application Priority Data
Oct. 25, 2010 (EP) .................... 10188695

(51) Int. Cl.
*G01J 5/02* (2006.01)
(52) U.S. Cl.
USPC .......................................... 250/343
(58) Field of Classification Search
USPC ................................. 250/342–352
See application file for complete search history.

(56) References Cited

U.S. PATENT DOCUMENTS

| | | | | |
|---|---|---|---|---|
| 5,070,245 A * | 12/1991 | Rantala et al. | ............... | 250/343 |
| 5,218,422 A | 6/1993 | Zoechbauer | | |
| 5,381,010 A * | 1/1995 | Gordon | ................... | 250/343 |
| 5,561,523 A | 10/1996 | Blomberg et al. | | |
| 5,646,729 A | 7/1997 | Koskinen et al. | | |
| 7,061,618 B2 | 6/2006 | Atia et al. | | |
| 7,091,487 B2 * | 8/2006 | Hodgkinson | ................ | 250/343 |
| 7,378,655 B2 * | 5/2008 | Tai et al. | ................... | 250/338.1 |
| 2003/0209669 A1 * | 11/2003 | Chou | ............................ | 250/343 |
| 2009/0146062 A1 * | 6/2009 | Russell | .................... | 250/339.13 |

FOREIGN PATENT DOCUMENTS

| EP | 1126256 A2 | 8/2001 |
|---|---|---|
| EP | 1482301 A1 | 12/2004 |
| WO | 2008/090261 A1 | 7/2008 |
| WO | 2010/112679 A1 | 10/2010 |

OTHER PUBLICATIONS

European Search Report and Written Opinion from EP Application No. 10188695.0 dated Apr. 4, 2011.

* cited by examiner

*Primary Examiner* — Kiho Kim
(74) *Attorney, Agent, or Firm* — Global Patent Operation; Marc A. Vivenzio

(57) ABSTRACT

A gas analyzer for measuring at least two components of a gas is disclosed herein. The gas analyzer comprising an emitter configured to emit infrared radiation through the gas, a filter assembly configured to permit a transmission of predetermined wavelengths emitted by the emitter, and a detector configured to receive wavelengths emitted by the emitter and penetrated through the filter assembly. The filter assembly comprises at least two tunable narrowband interference filters in series, each of the filters comprising two dielectric mirrors and an air space between the two dielectric mirrors to tune one of the filters to different transmission band than another of the filters.

19 Claims, 2 Drawing Sheets

GAS ANALYZER FOR MEASURING AT LEAST TWO COMPONENTS OF A GAS

BACKGROUND OF THE INVENTION

1. Field of the Invention

The field of the invention relates to a gas analyzer for measuring at least two components of a gas. The gas analyzer comprises an emitter for being able to emit infrared radiation through the gas, a filter assembly for allowing a transmission of predetermined wavelengths emitted by the emitter, and a detector for receiving wavelengths emitted by the emitter and penetrated through the filter assembly.

2. Description of Related Art

In anesthesia or in intensive care, the condition of a patient is often monitored e.g. by analyzing the gas exhaled by the patient for its content. For this reason either a small portion of the respiratory gas is delivered to a gas analyzer or the gas analyzer is directly connected to the respiratory circuit. In a non-dispersive infrared (NDIR) gas analyzer the measurement is based on the absorption of infrared (IR) radiation in the gas sample. A radiation source directs a beam of infrared radiation through a measuring chamber to a radiation detector whose output signal depends on the strength of the absorption of the radiation in the sample gas. The optical wavelength band used for the measurement is selected without dispersive elements such as a prism or a grating using an optical bandpass filter. The radiation source typically comprises an electrically heated filament or surface area and radiation collecting optics and emits radiation within a broad spectral region. The gas sample to be analyzed, i.e. the sample gas, is fed through the measuring chamber, whereupon the gas mixture is included in the chamber for analysis. The measuring chamber can be a tubular space provided with entrance and exit windows that are transparent at the measurement wavelength and with inlet and outlet for the sample gas. Radiation is absorbed by the gas sample when passing through the measuring chamber. The radiation detector generates an electrical signal that depends on the radiation power falling on its sensitive area. The detector type in a gas analyzer depends on its measurement wavelength. For measurement within a broad spectral range a thermal detector is convenient because its sensitivity only depends on the efficiency of the conversion of radiation to heat. To make the detector's output signal sensitive to a certain gas component, the wavelength band of the radiation coming to the detector is selected so that the gas component absorbs radiation within it. This selection is made using an optical bandpass filter whose bandwidth is typically 1%-2% of the center wavelength.

In NDIR multigas analyzers, the absorption of the gas sample is measured at several wavelength bands, selected to match the absorption spectra of the gas components of interest. This can be accomplished by using one radiation detector and by changing the optical bandpass filters on the optical path in succession. It is also possible to use several radiation detectors, combined with their corresponding bandpass filters. In addition to these measurement detectors, there may be one or more reference detectors. The reference detectors typically receive radiation from the radiation source at wavelength bands where the sample gas is known to have no or little absorption. To measure the strength of absorption, it is necessary to know the zero levels of the analyzer at the measure wavelengths. The zero level is the detector signal obtained at a wavelength when the sample gas does not absorb IR-radiation at that wavelength. The strength of absorption is calculated by forming the ratio between the zero level signal and the detector signal, supposing that absence of radiation results in a zero or otherwise known signal. It is possible to update the zero levels by separately measuring zero gas that is known to not absorb radiation at the measurement wavelengths. This method is commonly used in a sidestream configuration, where a gas sample is drawn from the respiratory circuit and analyzed separately.

It is also possible to obtain estimates for the zero levels without zeroing the analyzer with gas. This can be accomplished by the use of reference filters, whereupon the detector signals are measured at reference wavelengths where the gas sample is known not to absorb IR radiation. It is also possible to use separate reference detectors together with reference filters and use the output signals of the reference detectors as estimates for the zero levels at the measurement wavelengths. These estimates are continuously available together with the detector signals obtained at the measurement wavelengths. It is often sufficient to use one or two common reference wavelengths for all measurement wavelengths, especially if the measurement wavelengths are close to each other. The reference wavelengths can also be chosen is such a way that they can compensate for disturbing matters like water in liquid or gas form. This method is commonly used in a mainstream configuration where the analyzer is positioned to measure across the respiratory tube.

In the clinically used gas analyzer of mainstream type the whole volume or at least the main portion of the breathing air or gas mixture flows through the analyzer and its measuring chamber. Because the measuring chamber is in the breathing circuit, it is easily contaminated by mucus or condensed water. Thus, it is necessary to use one or more reference wavelengths in a mainstream analyzer in order to have good enough estimate for the zero level continuously available.

A clinical mainstream gas analyzer must be small, light, accurate and reliable. It is not possible to zero it during its normal operation. Yet, the analyzer must maintain its accuracy even if the measuring chamber would be contaminated. Due to these requirements, only single gas analyzers for carbon dioxide CO2 have been available and no really compact multigas analyzers of the mainstream type have been commercially available. The best construction would be a single path analyzer because then e.g. contamination of the measuring path would influence both measuring and reference wavelengths similarly and the effect on the gas concentration value would be eliminated. However, this is difficult to accomplish using a multiple of discrete bandpass filters. Either it would require a rotating filter wheel, which may be big and apt to mechanical damage, or a number of beam splitters to separate the different bandpass wavelengths to different detectors. Only the former method can make use of a single detector and thus avoid the problem of differences between separate detectors. However, with discrete dielectric optical bandpass filters it does not seem to be possible to make an analyzer small enough to apply also for patients like small children and neonates.

It is an additional problem that the different respiratory gases have so widely spaced wavelength regions of absorption. Carbon dioxide and nitrous oxide can be measured between 3900 nm and 4600 nm whereas all anesthetic agents absorb in the 8000 nm to 10000 nm region. The wavelength change of the transmission band of a dielectric IR filter with angle of incidence is, e.g., far too small to cover both ends of the wavelength region of interest. Therefore, such a single path solution would not be applicable.

Still another requirement is that the measurement has to be fast enough to measure the breathing curve. In practice, the rise time would have to be in the order of 200 ms. An interferometric analyzer for detection of substances can be a Fabry-Perot type interferometer with possibility of electrical modulation. Often the mirrors are closely spaced, but the distance is still several wavelengths. The free spectral range (FSR) may be only about 10 nm and the whole spectral region is covered by a large number of very narrow transmission peaks 10 nm apart. The free spectral range is the frequency or wavelength space between consecutive transmission peaks in the transmission spectrum of a Fabry-Perot interferometer. The SFR is inversely proportional to the distance between the reflective surfaces in the interferometer. The region of interest in this case must be chosen using discrete bandpass filters on a wheel. Thus, this solution cannot be made more compact or faster than an analyzer using only a filter wheel to select the measurement wavelengths.

A single path gas analyzer using a micromechanical and electrically tunable Fabry-Perot interferometer is well-known in the art. Contrary to the previous solution the resonator is very short, even as short as only half the wavelength of interest. This broadens the free spectral range of the interferometer. The analyzer can be made very compact but the construction allows wavelength tuning only within about 10% of a chosen wavelength. This makes measurements of multiple gases almost impossible unless the wavelength regions are close together.

Within the near infrared wavelength region up to about 1700 nm a solution with Fabry-Perot tunable filters in series is also known. A superluminescent light emitting diode is preferably used as source and either source and filters or filters and detector are integrated on an optical bench within a hermetic package. The use is primarily optical telecommunication. The filters are micromechanical with a free spectral range of about 200 nm, meaning that the space between the mirrors of the Fabry-Perot filter is a multitude (>3) of half the design wavelength.

BRIEF SUMMARY OF THE INVENTION

The above-mentioned shortcomings, disadvantages and problems are addressed herein which will be understood by reading and understanding the following specification.

One embodiment of the present invention provides a gas analyzer for measuring at least two components of a gas. The gas analyzer comprising an emitter configured to emit infrared radiation through the gas, a filter assembly configured to permit a transmission of predetermined wavelengths emitted by the emitter, and a detector configured to receive wavelengths emitted by the emitter and penetrated through the filter assembly. The filter assembly comprises at least two tunable narrowband interference filters in series, each of the filters comprising two dielectric mirrors and an air space between the two dielectric mirrors to tune one of the filters to different transmission band than another of the filters.

Various other features, objects, and advantages of the invention will be made apparent to those skilled in art from the accompanying drawings and detailed description thereof.

DETAILED DESCRIPTION OF THE INVENTION

Specific embodiments of the present invention are explained in the following detailed description making a reference to accompanying drawings. These detailed embodiments of the present invention can naturally be modified and should not limit the scope of the invention as set forth in the claims.

A gas analyzer for measuring at least two components of a gas such as a respiratory gas is described. An embodiment of the present invention can for instance be applied in clinical non-dispersive infrared multigas analyzers of mainstream type but it can also be applied in other types of respiratory gas analyzers and as well in gas analyzers to measure other gases than respiratory gases.

When measuring the patient gas, especially in neonatal and pediatric cases, it is crucial that the gas analyzer is fast, small and lightweight. A mainstream gas analyzer for only carbon dioxide and known in prior art can fulfill these criteria, but the problem arises when multiple gases are to be measured within often widely spaced wavelength regions. Gases with infrared absorption have their characteristic absorption regions and every gas component must be measured using at least one wavelength. Additionally, a reference must in most cases be established at a wavelength without or with little gas absorption to account for changes in the emitter radiation related to condensed water or other obstructing matter. The use of tunable narrowband filters according to an embodiment of the present invention enables measurement of multiple gases with infrared absorption and also an appropriate amount of references. Since the tunable wavelength region of one filter is fairy small and the typical out of band transmission must be blocked, two tunable narrowband filters normally have to be used as an assembly to allow for measurement within a wavelength region that covers both carbon dioxide and anesthetic agents. Still the construction is very compact and can be adapted to the amount of gases measured.

The benefit of using the non-dispersive measurement arrangement according to the embodiment of the present invention is that a true single path measurement is possible. This means that only one emitter and one detector is necessary to measure gases at multiple wavelengths. The signals from the detector represents in succession both the gases to be measured and the references needed for signal correction. The tunable narrowband filters are preferably made using silicon micromechanics.

Figure 1:
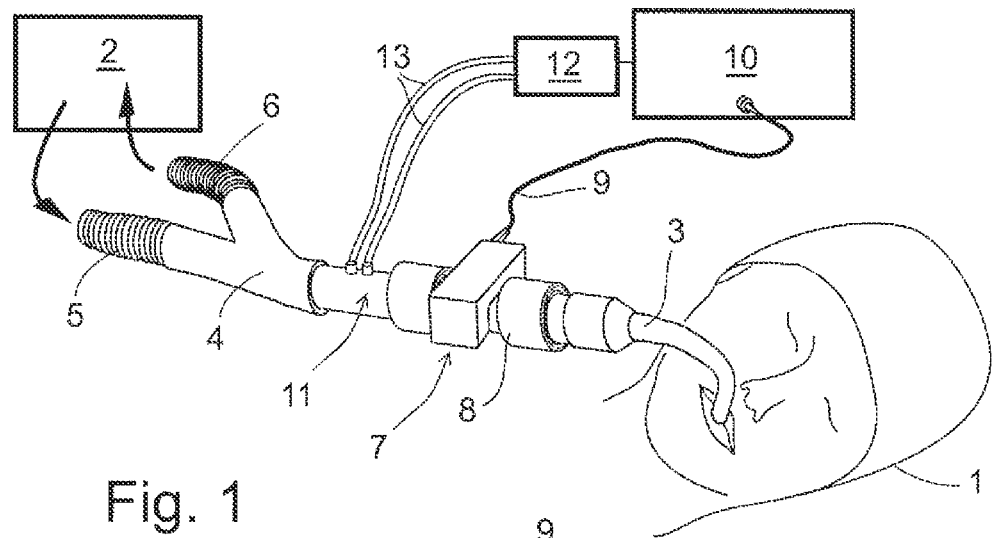
FIG. 1 illustrates a medical mainstream gas analyzer connected to the ventilation circuit of a patient.

Preferably this analyzer is measuring directly across the respiratory tube of an intubated patient. Such a respiratory circuit with a medical gas analyzer is shown in FIG. 1. A patient 1 is connected to a ventilator 2 using an intubation tube 3, a Y-piece 4, an inspiratory limb 5 and an expiratory limb 6. A gas analyzer 7 which may comprise an adapter 8 is connected to the intubation tube. The gas analyzer 7 in FIG. 1 is a so called mainstream gas analyzer measuring gases flowing between the ventilator 2 and the patient 1 without withdrawing samples of the gas to a separate gas analyzer such as a sidestream gas analyzer at a distance from the flow between the ventilator 2 and the patient 1. Naturally this same gas analyzer technology can also be exploited in sidestream gas analyzers. The analyzer shown in FIG. 1 is electrically connected via cable 9 to the patient monitor 10. The gases measured are at least carbon dioxide but may also be oxygen, nitrous oxide or any the volatile anesthetic agents halothane, enflurane, isoflurane, desflurane and sevoflurane. Additionally, there may be a spirometry adapter 11 for measuring the gas flow in the respiratory circuit. In this example the sensor 12 is located at the distal end of two pressure relying tubes 13. The spirometry sensor may be separately connected as in FIG. 1 or it can be integrated into the mainstream gas analyzer.

Figure 2:
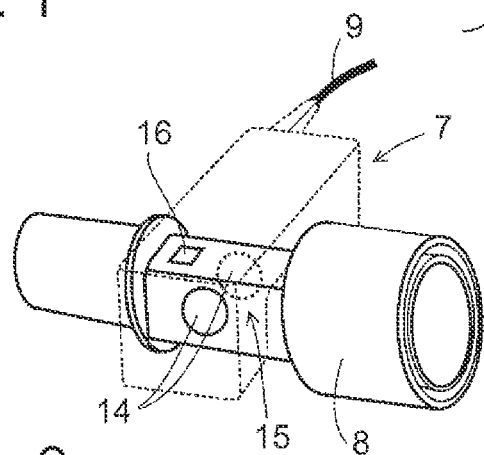
FIG. 2 shows the measuring adapter of the gas analyzer.

In FIG. 2 a close-up of the gas analyzer 7 is depicted in order to better show the construction of the adapter 8, which normally may be disposable. It is provided with at least one optical window 14 for allowing the infrared radiation to be absorbed due to the gas components. Typically there are two infrared transmitting optical windows 14. The infrared emitter is located on one side of the adapter and the non-dispersive filter assembly and detector or detectors on the opposite side in such a way the infrared radiation is directed from the emitter through the windows and respective narrowband filters to a detector. The signal from the detector is amplified and modified to reflect the concentration of the gas to be measured or it may be a measurement at a reference wavelength with no or little gas absorption. As mentioned above, respiratory gases can be carbon dioxide, nitrous oxide and different volatile anesthetic agents. All these gases absorb infrared radiation within some specific wavelength region and this region is selected using the narrowband filter as will be explained later. Gases like oxygen, that do not absorb enough infrared radiation in a measuring channel 15 between the optical windows 14, which measuring channel is typically short, which is less than 10 mm, must be measured using a separate sensor 16. This sensor can be e.g. a chemical fuel cell or it can be based on luminescence quenching. The measuring channel can be part of the gas analyzer and is typically also part of the adapter 8.

Figure 3:
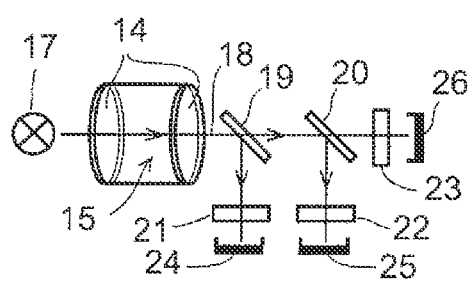
FIG. 3 shows the optical principle of one type of prior art multigas analyzer.

The mainstream sensors on the market have mostly measured only one gas, carbon dioxide. Mechanical and optical problems arise if multiple gases are to be measured. One type of prior art analyzer is schematically presented in FIG. 3. It is able to measure two different gases using a common reference. From an emitter 17 for being able to emit infrared radiation a broadband beam of a radiation 18 is directed via the measuring channel 15 with windows 14 to the detector assembly comprising two beam splitters, 19 and 20, three narrowband filters 21, 22 and 23 and three detectors 24, 25 and 26. One of the filter-detector pair measures a reference signal, e.g. the detector 24 with the filter 21, via the beam splitter 19. The transmission of the filter 21 is chosen so that it does not have or has minimal infrared absorption for any of the gases in the mixture flowing in the measuring channel 15. The signal from the detector 24 can then be used to monitor fluctuations in the infrared radiation 18 not related to gas absorption. Typically these arise from a condensation of water droplets or a deposition of an absorbing material like a mucus or blood on optical windows 14. Fluctuations in the radiation 18 from the emitter 17 are also monitored. Further, this reference signal is used to correct the measurement signals from the two other detectors 25 and 26. The portion of the radiation transmitted through the beam splitter 19 proceeds to the beam splitter 20. Using the beam splitter 20 the radiation is divided into two measuring beams and two different gases can be measured using the filter-detector pair 22/25 and 23/26. These gases could be e.g. carbon dioxide and nitrous oxide. It is not very easy to add more filter-detector pairs to this configuration. The size will grow and the usable signal is gradually reduced. For this reason the analyzer is usually designed to measure only one gas component with infrared absorption.

Figure 4:
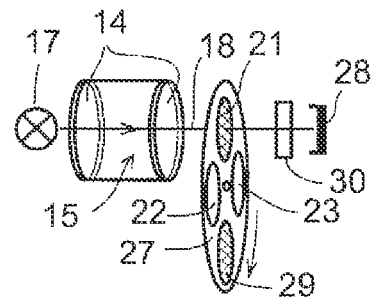
FIG. 4 shows the optical principle of another type of prior art multigas analyzer.

Several gas components with infrared absorption can easier be measured using a configuration depicted in FIG. 4. The emitter 17, the measuring channel 15 with windows 14 and the beam of radiation are similar to those in FIG. 3 but instead of a beam splitter a rotating filter wheel 27 is used to exchange the different filters in front of a single detector 28. In this prior art example the same filters 21, 22 and 23 can be used and, additionally, a filter 29. This filter 29 can be a second reference filter or it can be a measuring filter for a third gas. An additional filter 30 may have to be used to block unwanted radiation from outside the measuring wavelength regions. This analyzer can be made fairly compact but has the drawback of delicate moving parts. A multiple of filters can in principle be mounted on the filter wheel 27 but for measurement of all the patient gases with infrared absorption mentioned above it would take a minimum of seven measuring filters and two reference filters. With nine filters the size of the filter wheel already sets limitations regarding how small the analyzer can be constructed.

Figure 5:
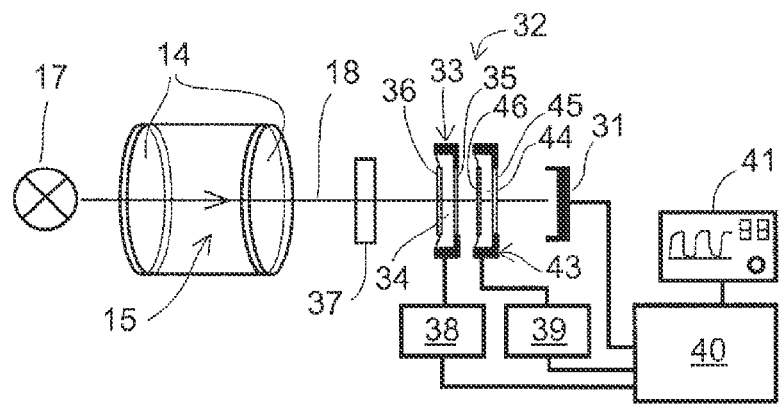
FIG. 5 shows the optical principle of a multigas analyzer according to an embodiment of the present invention.

A construction of the gas analyzer according to one embodiment of the present invention is shown in FIG. 5. Like in the prior art it comprises an emitter 17 such as an infrared broadband source, which emits a beam of infrared radiation 18 through a gas in a measuring channel 15 having at least one optical window 14. The measuring channel may be part of the adapter, mountable in an airway between a ventilator 2 for assisting a ventilation of a patient 1, and an intubation tube 3 connecting the ventilator to lungs of the patient. The adapter 8 may be detachable from other components of the gas analyzer. Also the gas analyzer comprises a filter assembly 32 and a detector 32. The beam of radiation hits a detector 31 after penetrating a filter assembly 32 comprising two tunable narrowband interference filters 33 and 43 connected in series. These two filters are preferably located close to the detector 31 but could also be mounted in connection with the emitter 17. The filters typically are tunable Fabry-Perot filters with an electrically tunable air space 34, 44 between two dielectric mirrors 35, 45 and 36, 46. Normally, one of these mirrors 35, 45 is fixed and the other 36, 47 is adjustable. The adjustment or tuning is usually accomplished using mechanical means like a micrometer screw or a piezoelectric motor. Preferably in this case, the filters are made using well-known micromechanical silicon technique. Then it is more feasible to tune the air space 34, 44 electrically, e.g. using electric field or magnetic field. Each interference filter 33 and 43 needs its own electronic driver 38 and 39 respectively. A processor 40 controls the electronic drivers to tune the air space of the interference filters and also records the signal from detector 31 and further processes the data into one of qualitative and quantitative result. These all may be parts of the gas analyzer 7. The quantitative result may be a concentration reading at the output. The qualitative result is needed to identify the presence of some gas components. A display unit 41 is connected to the processor 40 to show gas concentrations and/or respiratory graphs. The different parts could either be located within the gas analyzer 7 or some parts could be in a host instrument like the patient monitor 10. Gas analyzer 7 is normally detachable from the patient monitor 10.

Technically, the interference filter may be a Fabry-Perot interferometer with an air space between two closely spaced, at least in some wavelength region highly reflective parallel mirror plates. Especially the adjustable mirror 36, 46 is very thin and comprises a number of dielectric layers with a thickness of normally less than the design wavelength. The mirror 36, 46 is parallel to mirror 35, 45 in a relatively small usable central region of the interference filter 33, 43. The transmission spectrum exhibits one or several narrow peaks of high transmission corresponding to optical resonances between the mirrors. The air space or distance between the mirrors is preferably of the first order, meaning one half the wavelength of the narrow transmission band. For the second and third order filter with an air space of one wavelength (2 halves) or 3/2 wavelengths (3 halves), additional transmission bands are introduced in the spectrum and except for possible special cases there is no use for these when measuring patient gases. Higher order interference filters are not considered beneficial so an order less than four is preferable. The absorption regions of different patient gases are mainly in two wavelength regions, 3.9-4.6 µm, more spesifically 4.2-4.6 µm, for carbon dioxide and nitrous oxide and 8.0-10.0 µm, more spesifically 8.2-8.9 µm for the different anesthetic agents. Carbon dioxide and nitrous oxide both have discrete and selective wavelengths (4.3 µm and 3.9 or 4.5 µm, respectively) whereas all the anesthetic agents absorb at some wavelength within the region 8.2-8.9 µm. Since there are a maximum of five anesthetic agents in use, a minimum of five different wavelengths must be used in the measurements. Another possibility would be to scan the whole wavelength region and record the spectrum with appropriate wavelength resolution.

Those two wavelength regions of interest in the case of respiratory gases are spaced apart with close to a factor of two and this fact limits the possible solutions if one wants to measure both regions using a single radiation path and a single detector. Even if one tunable Fabry-Perot filter could be adjusted from the higher wavelength region down to the lower one, a narrowband transmission region is impossible to achieve at all wavelengths. With metallic broadband mirrors in the Fabry-Perot filter there will always be additional transmission bands on the short wavelength side of the spectrum. If the filter is tuned to 8.6 µm for measurement of anesthetic agents it will also have a transmission band at 4.3 µm where carbon dioxide absorbs. That band would have to be removed using a second tunable Fabry-Perot filter with metallic mirrors but this filter would then also reduce the transmission at the upper transmission band so a practical solution is not possible to construct. The situation changes when using dielectric mirrors on each side of the air space of the Fabry-Perot filter.

Because of wavelength interference also in the mirror layers there will be transmission bands also at wavelengths that do not fulfill the criteria of a multiple of half wavelengths of interest. There will also be a transmission at wavelength regions higher than the wavelength of interest. Then it becomes possible to remove unwanted transmission bands of one interference filter using a second interference filter without introducing disturbing wavelength regions or reducing the transmission of the wavelength regions in use for gas measurements. In summary, using two tunable dielectric interference filters in series enable the measurement of widely spaced absorption regions. The long wavelength region can have a wavelength 20% or more longer than the short wavelength region. For respiratory gases the factor was about two (100%) as mentioned above.

Figure 6:
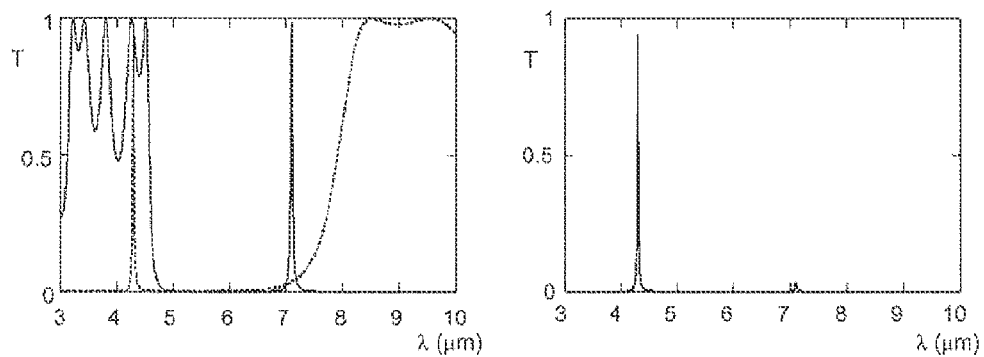
FIG. 6 shows the infrared transmission spectrum of two separate tunable narrowband interference filters (left) shown in FIG. 5 and the spectrum of those filters combined in series (right) in one tuned situation according to an embodiment of the present invention.

A typical spectral situation is shown in the two graphs of FIG. 6. The transmission spectrum as a function of wavelength in µm on the left side presents the transmission bands of filters 33 and 43 as taken separately and the right spectrum shows the transmission of the filter combination. In this example carbon dioxide at 4.3 µm would be measured using detector 31. The order of filters 33 and 43 along the radiation beam 18 is not critical if optical leaks around the filters to the detector can be avoided. In this case it may be beneficial to remove most of the longer wavelength spectrum first using the tunable narrowband interference filter with transmission shown as a continuous line and then use the other tunable narrowband interference filter with a dashed appearance. Thus, most of the broadband heat radiation possibly leaking to the detector 31 is reflected away from the radiation path. The design wavelengths of the dielectric mirrors in this example are 6.85 µm and 3.75 µm, respectively. Both wavelengths are shorter than the mentioned wavelength region of interest. With design wavelength is meant the wavelength at which most of the dielectric layers have an optical thickness of a quarter of this wavelength. For a dense optical medium optical thickness means a thickness of wavelength divided by the refractive index of this medium. The chosen design wavelength depends on the refractive index of the different layers in the mirrors.

The combined filter also has to be able to block either the higher or the lower wavelength region of interest and the design wavelengths are chosen according to this requirement. The air space of the filters are electrically tunable and do not have this specific design wavelength. However, the preferable thickness of the air space is of the order of half the wavelength of the wavelength of interest. For all the reasons mentioned above, in most cases there will be an interferometric mismatch in the filter, meaning that the filter bandpass wavelength is not exactly at an air space distance of half of this wavelength. For the filters in FIG. 6 the air space 34, 44 has a thickness of 3.6 µm and 2.225 µm, respectively, even if the transmission bands are not exactly at wavelengths twice these values. This feature is beneficial and makes it possible to block either the wavelength region 8-9 µm as in FIG. 6 or the wavelength region 3.9-4.6 µm as in FIG. 7. The thickness of the air space 34, 44 in this example of the same filter combination as in FIG. 6 is 4.45 µm and 1.85 µm, respectively. The combined filter in the right spectrum gives a transmission band at about 8.38 µm, suitable as one wavelength for measuring anesthetic agents. The small transmission below 4 µm is unavoidable but this disturbing transmission penetratable by the tunable narrowband interference filters can easily be filtered out using a dielectric highpass filter 37 as shown in FIG. 5, with a cut-on wavelength of about 3.9 µm.

Figure 7:
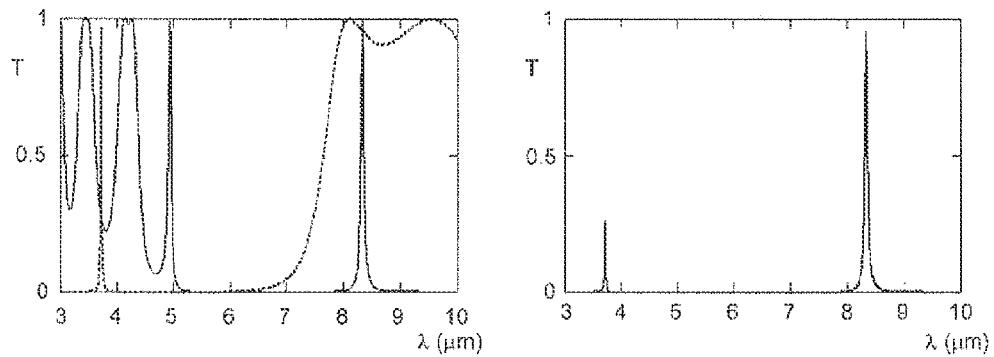
FIG. 7 shows the infrared transmission spectrum of the two filters in FIG. 6 in another tuned situation according to an embodiment of the present invention.

The filter transmission spectra in FIGS. 6 and 7 are examples of the two tunable narrowband interference filters 33 and 43 in the filter assembly 32. Other combinations and design wavelengths can be used according to the intended use. The transmission regions shown are regions where the gases to be measured have absorption. However, it is easy to adjust the filter combination to an adjacent wavelength position with no gas absorption in order to establish a reference signal. All different gas and reference measurement signals are recorder in succession and the compensated gas concentrations are calculated and displayed in accordance with well-known principles.

In conclusion, compared to a gas sensor with several discrete detectors and filters the described solution both saves money and space because fewer components and no beam splitters are needed. Also, no moving parts e.g. in the form of a filter wheel is needed. The filter assembly 32 and detector 31 can be assembled in one package reducing the need for factory labor considerably. Because the filter assembly 32 is continuously tunable using electronics it is possible to adapt its function to any change in needed spectral response. The gas analyzer is a true IR single path photometer for measuring all respiratory gases with IR absorption and corresponding references, especially in a mainstream configuration and because of the compact construction also for measuring neonatal respiratory gases. In addition to carbon dioxide, also gas absorption within the wavelength region 8-10 μm will be possible to measure, enabling the measurement of all anesthetic agents in use today. It may also be possible to add a third tunable narrowband interference filter to be used for chopping the optical signal. Patient gases can be measured also in a sidestream configuration where a gas sample is drawn using a pump and analyzed separately from the respiratory circuit. The gas analyzer could also be connected e.g. to a nasal cannula and it could be possible to measure the respiratory gas from spontaneously breathing patients in addition to ventilated patients.

The written description uses examples to disclose the embodiments of the present invention, including the best mode, and also to enable any person skilled in the art to make and use the invention. The patentable scope of the embodiments of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A gas analyzer for measuring at least two components of a gas, the gas analyzer comprising:
   an emitter that emits infrared radiation through the gas;
   a filter assembly configured to permit a transmission of predetermined wavelengths emitted by the emitter;
   a detector configured to receive wavelengths emitted by the emitter and penetrated through the filter assembly;
   the filter assembly comprising at least two tunable narrowband interference filters in series, each of the filters comprising two dielectric mirrors and an air space between the two dielectric mirrors, one of the filters being tuned to a different transmission band than another of the filters; and
   a dielectric highpass filter to filter out disturbing transmissions penetrable by the at least two tunable narrowband interference filters.

2. The gas analyzer according to claim 1 further comprising a measuring channel, wherein the measuring channel comprises at least one optical window configured to permit the infrared radiation to be absorbed due to the gas components.

3. The gas analyzer according to claim 2, wherein the measuring channel is part of an adapter, mountable in an airway between a ventilator configured to assist a ventilation of a patient, and an intubation tube connecting the ventilator to lungs of the patient.

4. The gas analyzer according to claim 3, wherein the adapter is detachable from other components of the gas analyzer.

5. The gas analyzer according to claim 1 further comprising electronic drivers for each of the at least two tunable narrowband interference filters, the electronic drivers configured to tune the air space between the two dielectric mirrors.

6. The gas analyzer according to claim 5, wherein the air space is electrical tunable using electric field or magnetic field.

7. The gas analyzer according to claim 5 further comprising a processor configured to control the electronic drivers to tune the air space between the two dielectric minors.

8. The gas analyzer according to claim 7, wherein the processor together with a display unit is also configured to record a signal received from the detector and to process a data of the signal producing one of a qualitative and quantitative result.

9. The gas analyzer according to claim 1, wherein the two dielectric mirrors of the narrowband interference filter are highly reflective parallel plates.

10. The gas analyzer according to claim 1, wherein a distance between the two dielectric mirrors in the air space is such that the interference filter is of less than a fourth order.

11. The gas analyzer according to claim 1, wherein a distance between the two dielectric mirrors in the air space is one half the wavelength of the narrow transmission band which is an interference filter of a first order.

12. The gas analyzer according, to claim 1, comprising a single detector making possible only a single radiation path in the gas analyzer.

13. The gas analyzer according to claim 1, wherein a transmission below about 4.0 μm is filtered out using the dielectric highpass filter.

14. The gas analyzer according to claim 1, wherein the two tunable narrowband interference filters in series are used to allow radiation penetration within a wavelength region of about 8.0 μm to about 10.0 μm, for the measurement of at least one anesthetic agent.

15. The gas analyzer of claim 1, wherein the two tunable narrowband interference filters in series are used to allow radiation penetration within a wavelength region of about 8.2 μm to about 8.9 μm for the measurement of at least one anesthetic agent.

16. The gas analyzer of claim 1, wherein the two tunable narrowband interference filters in series are used to allow radiation penetration within a wavelength region of about 3.9 μm to about 4.6 μm for the measurement of at least one of carbon dioxide and nitrous oxide.

17. The gas analyzer of claim 1, wherein the two tunable narrowband interference filters in series are used to allow radiation penetration within a wavelength region of about 4.2 μm to about 4.6 μm for the measurement of at least one of carbon dioxide and nitrous oxide.

18. The gas analyzer according to claim 1, wherein tuning one of the filters to a different transmission band than another of the filters enables to block a wavelength region of about 8.0 μm to about 10.0 μm, for the measurement of at least one anesthetic agent.

19. The gas analyzer according to claim 1, wherein tuning one of the filters to a different transmission band than another of the filters enables to block a wavelength region of about 3.9 μm to about 4.6 μm, for the measurement of at least one of carbon dioxide and nitrous oxide.

* * * * *

UNITED STATES PATENT AND TRADEMARK OFFICE
CERTIFICATE OF CORRECTION

PATENT NO. : 8,642,966 B2  
APPLICATION NO. : 13/280852  
DATED : February 4, 2014  
INVENTOR(S) : Weckstrom et al.

Page 1 of 1

It is certified that error appears in the above-identified patent and that said Letters Patent is hereby corrected as shown below:

In the Claims:

In Column 10, Line 2, in Claim 6, delete "electrical" and insert -- electrically --, therefor.

In Column 10, Line 6, in Claim 7, delete "minors." and insert -- mirrors. --, therefor.

In Column 10, Line 23, in Claim 12, delete "according," and insert -- according --, therefor.

Signed and Sealed this
Twentieth Day of May, 2014

Michelle K. Lee
*Deputy Director of the United States Patent and Trademark Office*